United States Patent
Nishimura et al.

(10) Patent No.: US 9,439,817 B2
(45) Date of Patent: Sep. 13, 2016

(54) ABSORBENT ARTICLE AND METHOD FOR PRODUCING THE SAME

(75) Inventors: Kiyoko Nishimura, Kagawa (JP); Toshiyuki Tanio, Kagawa (JP); Azusa Matsushima, Kagawa (JP)

(73) Assignee: Unicharm Corporation, Ehime (JP)

( * ) Notice: Subject to any disclaimer, the term of this patent is extended or adjusted under 35 U.S.C. 154(b) by 83 days.

(21) Appl. No.: 14/130,172

(22) PCT Filed: Jun. 7, 2012

(86) PCT No.: PCT/JP2012/064655
§ 371 (c)(1),
(2), (4) Date: Dec. 30, 2013

(87) PCT Pub. No.: WO2013/018433
PCT Pub. Date: Feb. 7, 2013

(65) Prior Publication Data
US 2014/0155852 A1     Jun. 5, 2014

(30) Foreign Application Priority Data
Jul. 29, 2011 (JP) ................................ 2011-167750

(51) Int. Cl.
*A61F 13/56* (2006.01)
*A61F 13/15* (2006.01)

(52) U.S. Cl.
CPC ...... *A61F 13/5611* (2013.01); *A61F 13/15211* (2013.01); *A61F 13/15699* (2013.01); *Y10T 156/1052* (2015.01)

(58) Field of Classification Search
CPC ............. A61F 13/15211; A61F 13/56; A61F 13/5605; A61F 13/5611; A61F 13/5616; A61F 2013/51429
USPC ............................ 604/385.22, 386, 387, 389
See application file for complete search history.

(56) References Cited

U.S. PATENT DOCUMENTS

| | | | |
|---|---|---|---|
| 3,688,771 A | 9/1972 | Werner | |
| 4,690,680 A * | 9/1987 | Higgins | 604/386 |

(Continued)

FOREIGN PATENT DOCUMENTS

| | | |
|---|---|---|
| EP | 2 184 045 A1 | 5/2010 |
| EP | 2 272 477 A1 | 1/2011 |

(Continued)

OTHER PUBLICATIONS

International Search Report from corresponding PCT application No. PCT/JP2012/064655 dated Aug. 14, 2012 (4 pgs).

(Continued)

*Primary Examiner* — Peter S Vasat
(74) *Attorney, Agent, or Firm* — Brinks Gilson & Lione

(57) ABSTRACT

A water-disintegrable absorbent article adapted to be easily peeled off the wearer's undergarment after use. A pantiliner has a topsheet lying on a body side of the wearer, a backsheet and a liquid-absorbent body interposed between the top- and backsheets. The backsheet may be formed of a water-disintegrable fibrous nonwoven fabric of which the component fibers have an orientation extending in a longitudinal direction. On a non-body side, first adhesive regions adapted to be attached to the wearer's undergarment and second adhesive regions allocated on both outer sides in a transverse direction of the first adhesive regions so as to be spaced in the transverse direction from the first adhesive regions. The first adhesive regions include front first adhesive regions, rear first adhesive regions and central first adhesive regions allocated between the front and rear first adhesive regions spaced apart from each other in the longitudinal direction. The second adhesive regions include front second adhesive regions and rear second adhesive regions spaced apart from each other in the longitudinal direction. The central first adhesive regions are allocated in a space area defined by the front and rear second adhesive regions and arranged in the transverse direction.

17 Claims, 6 Drawing Sheets

(56) References Cited

U.S. PATENT DOCUMENTS

| | | | |
|---|---|---|---|
| 6,432,095 B1* | 8/2002 | Wada et al. | 604/385.01 |
| 2003/0163109 A1 | 8/2003 | Ohba et al. | |
| 2009/0062761 A1* | 3/2009 | Goerg-Wood et al. | 604/385.01 |
| 2010/0256585 A1* | 10/2010 | Konawa | 604/385.04 |
| 2011/0144607 A1 | 6/2011 | Suzuki et al. | |
| 2011/0184363 A1* | 7/2011 | Suzuki et al. | 604/364 |

FOREIGN PATENT DOCUMENTS

| | | |
|---|---|---|
| EP | 2 292 201 A1 | 3/2011 |
| JP | 6-500485 | 1/1994 |
| JP | 11-504846 | 5/1999 |
| JP | 2001-145669 | 5/2001 |
| JP | 2005-518251 A | 6/2005 |
| JP | 2005-319333 | 11/2005 |
| JP | 2009-268537 | 11/2009 |
| JP | 2011/139847 | 7/2011 |
| WO | WO 92/04000 | 3/1992 |
| WO | WO 97/31604 | 9/1997 |
| WO | WO 2009/157476 A1 | 12/2009 |

OTHER PUBLICATIONS

Supplementary European Search Report from corresponding European application No. 12819796.9 dated Apr. 7, 2015 (8 pgs).

* cited by examiner

ABSORBENT ARTICLE AND METHOD FOR PRODUCING THE SAME

RELATED APPLICATION

This application is a 35 U.S.C. §371 national phase filing of International Patent Application No. PCT/JP2012/064655, filed Jun. 7, 2012, through which and to which priority is claimed under 35 U.S.C. §119 to Japanese Patent Application No. 2011-167750, filed Jul. 29, 2011.

TECHNICAL FIELD

The present invention relates to absorbent articles and methods for producing the same and more specifically to water-disintegrable sanitary napkins, pantiliners and urine-absorbent pads and methods for producing the same.

BACKGROUND

Conventionally, sanitary napkins or pantiliners as examples of the water-disintegrable absorbent articles are known. For example, patent literature 1 discloses the absorbent article having a topsheet, a backsheet and an absorbent layer interposed between the top- and backsheets. As material for the topsheet and the backsheet, water-disintegrable fibrous nonwoven fabric is used in this known absorbent article. On the lower surface of the backsheet, pressure-sensitive adhesive regions are formed. This absorbent article as a whole is water-disintegrable and piping system should not be clogged after the used article has been disposed into flushing water of a lavatory.

CITATION LIST

Patent Literature

{PTL 1}: JP 3748022 B

SUMMARY

Technical Problem

In the absorbent article disclosed in PTL 1, a plurality of the adhesive regions is formed so as to be spaced apart from each other in the longitudinal direction as well as in the transverse direction. Each of these adhesive regions has a circular shape of which the diameter is in a range of 10 mm to 1 mm. Such small adhesive regions have weak adhesive strength and, to compensate this, pressure-sensitive adhesive agent of high adhesive strength should be used. As a result, the backsheet of such absorbent article is attached to the wearer's undergarment too tightly and, when the wearer tries to peel off the article from the undergarment after used, the component fibers in the fibrous nonwoven fabric as material for the backsheet might dissociate from the backsheet and left on the undergarment together with the pressure-sensitive adhesive agent.

An object of the present invention is to provide an absorbent article improved to be easily peeled off the wearer's undergarment after used.

Solution to Problem

The present invention includes first and second aspects. The first aspect relates to an absorbent article having a longitudinal direction and a transverse direction and including a body-side, a non-body-side opposite to the body-side, a water-disintegrable topsheet lying on the body-side, a water-disintegrable backsheet lying on the non-body-side, a water-disintegrable body-fluid absorbent body interposed between these top- and backsheets, and adhesive regions formed on the non-body-side of the backsheet and through which the backsheet is attachable to a wearer's undergarment.

In the absorbent article, the backsheet is formed of a fibrous nonwoven fabric of which component fibers have an orientation extending in the longitudinal direction, the adhesive regions include first adhesive regions extending in the longitudinal direction and second adhesive regions allocated on both outer sides in the transverse direction of the first adhesive regions so as to be spaced apart from the first adhesive regions in the transverse direction and at least part of the first adhesive regions is allocated in a space area defined in the longitudinal direction between the second adhesive regions.

As used herein, the expression "the absorbent article is attachable to the wearer's undergarment" means that the absorbent article may be attached to the wearer's undergarment through the adhesive regions and, after used, the article may be peeled off the wearer's undergarment. It is suggested by this expression that adhesive strength may be at a level allowing the article once attached to the wearer's undergarment to be easily peeled off the wearer's undergarment after used. For the adhesive regions, a pressure-sensitive adhesive agent may be used.

The second aspect relates to a method of producing the absorbent article as described above. Namely, a method for producing the absorbent article including the steps of: transporting a first fibrous web in a machine direction; laminating an absorbent web on the first fibrous web and securing them to each other; laminating a second fibrous web on the first fibrous web through the absorbent web and securing them to each other; forming adhesive regions on a surface of one of the first fibrous web and the second fibrous web opposite to the absorbent web; laminating a release sheet on the adhesive regions; and cutting a laminate composed of the first and second fibrous webs, the absorbent web and the release sheet.

In the method for producing the absorbent article, an adhesive coater having first nozzles arranged in the cross direction being orthogonal to the machine direction and second nozzles allocated on the both outsides in the cross direction of the first nozzles distributes an adhesive agent at some intervals and thereby forms the adhesive regions.

As used herein, the term "water-disintegrable sheet" means a fibrous nonwoven fabric sheet formed of component fibers having a fiber length of 7 mm or less and oriented so that a mechanical entanglement of the fibers may be broken up in flushing water of the lavatory.

Advantageous Effects of Invention

According to one or more embodiments of the present invention, since the first and second adhesive regions are formed on the backsheet so as to extend in the longitudinal direction, some of the fibers underlying the first and second adhesive regions of the backsheet should not dissociate from the backsheet and adhered to the wearer's undergarment together with the adhesive agent. The arrangement that the first adhesive regions are allocated also in the space area defined by the second adhesive regions spaced apart from each other in the longitudinal direction is effective to prevent the portions of the backsheet including the first and second adhesive regions from being entangled with each other and forming a chunk possibly causing the piping system to become clogged.

DESCRIPTION OF EMBODIMENTS

Figure 1:
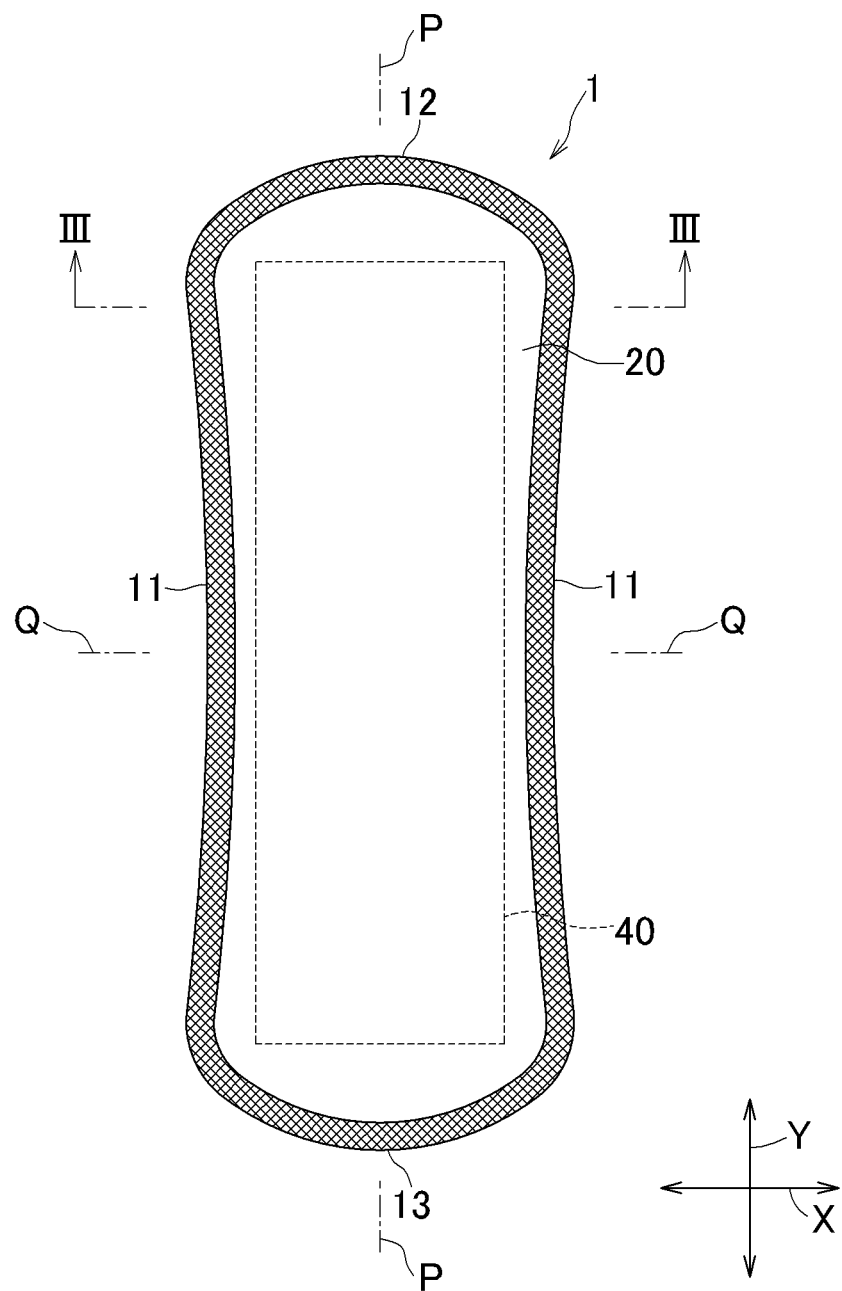
FIG. 1 is a plan view of a pantiliner as an embodiment of the absorbent articles.
Figure 2:
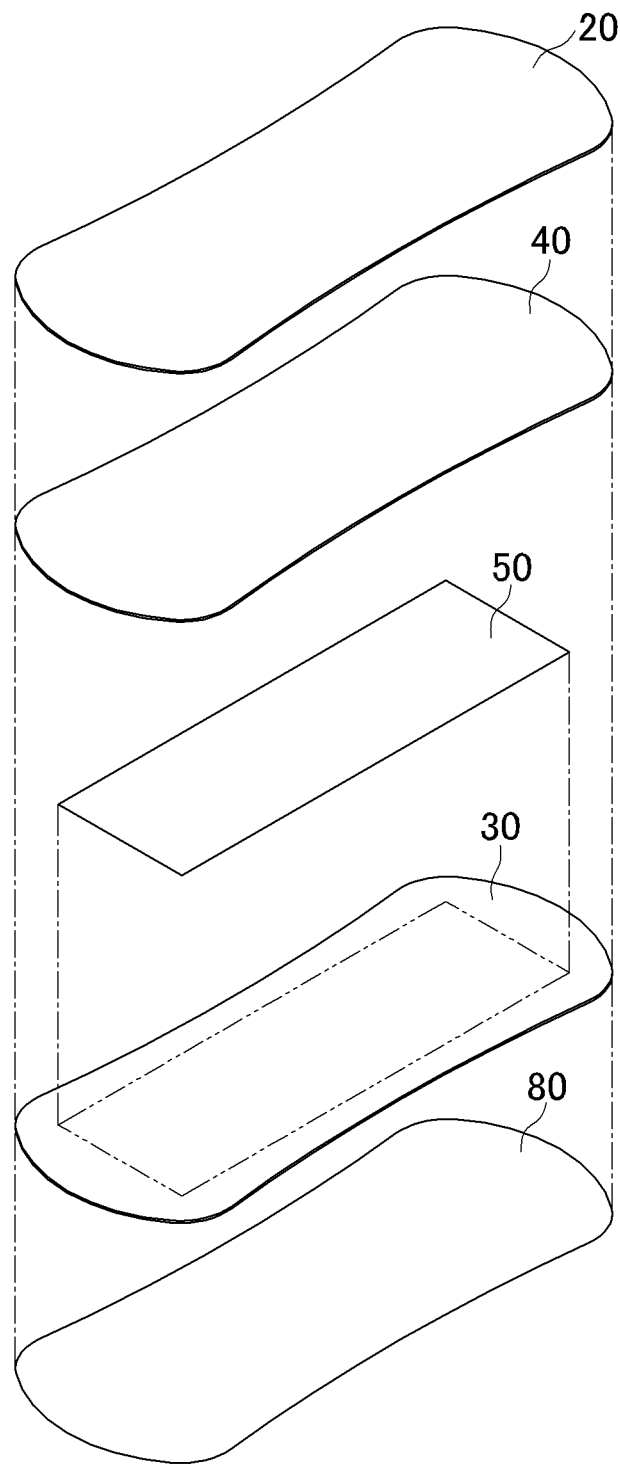
FIG. 2 is an exploded perspective view of the pantiliner.
Figure 3:
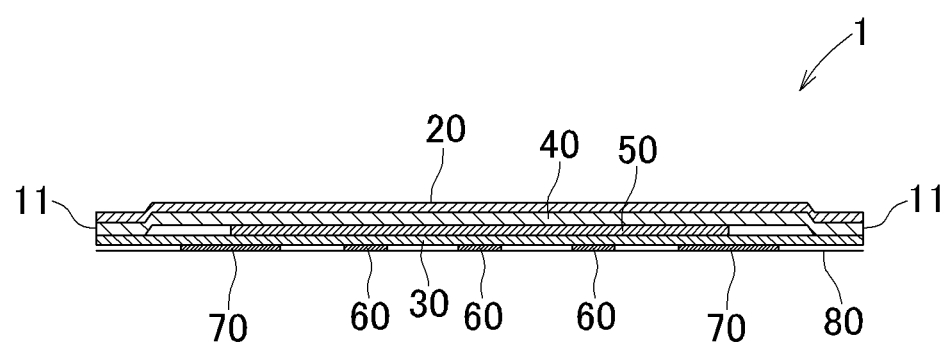
FIG. 3 is a sectional view taken along line III-III in FIG. 1.
Figure 4:
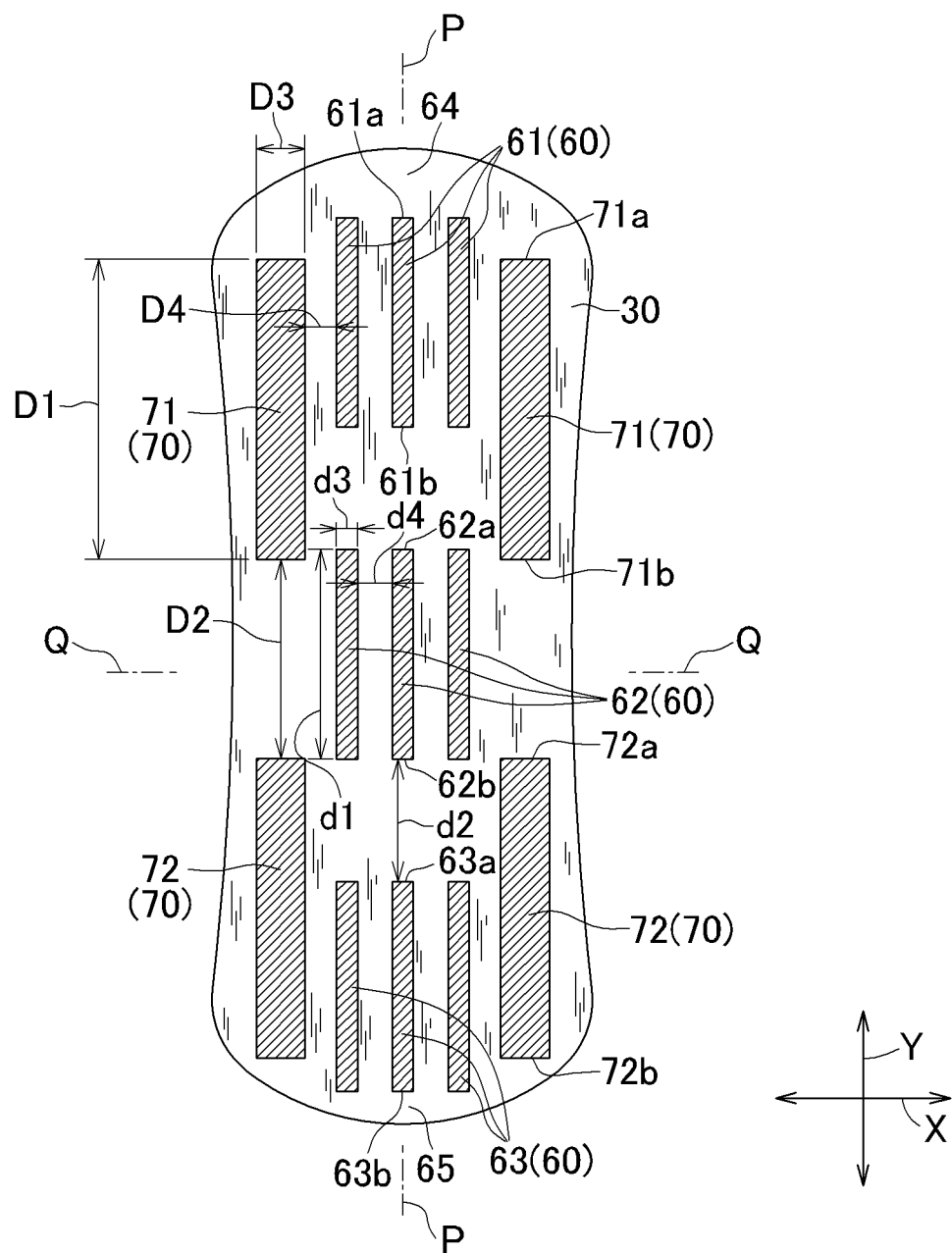
FIG. 4 is a plan view of the pantiliner as viewed from the side of a backsheet thereof.

FIG. 1 is a plan view of a pantiliner 1 as an example of the absorbent articles according to the present invention as viewed from the side of a topsheet 20, FIG. 2 is an exploded perspective view of the pantiliner 1, FIG. 3 is a sectional view taken along line III-III in FIG. 1 and FIG. 4 is a plan view of the pantiliner 1 as viewed from the side of a backsheet 30 thereof. For convenience of illustration, FIG. 4 illustrates adhesive zones in an exposed state after a release sheet 80 has been peeled off.

As illustrated in FIGS. 1 through 4, the pantiliner 1 has a longitudinal direction Y, a transverse direction X being orthogonal to the longitudinal direction Y, an imaginary longitudinal center line P-P bisecting a dimension in the transverse direction X and an imaginary transverse center line Q-Q bisecting a dimension in the longitudinal direction Y. Both side edges 11 extending in the longitudinal direction Y are curved inwardly in such a manner that a spacing between these side edges 11 gradually decreases as these side edges 11 come closer to the imaginary transverse center line Q-Q. Front and rear ends 12, 13 extending in the transverse direction X are curved in such a manner that a spacing between these both ends 12, 13 gradually increases, namely, the respective ends 12, 13 become convex outwardly as these both ends 12, 13 come closer to the imaginary longitudinal center line P-P.

The pantiliner 1 includes the topsheet 20 adapted to extend on the wearer's body side, the backsheet 30 adapted to extend on the non-body-side opposite to the wearer's body side (the side of the wearer's undergarment), a bodily fluid absorbent body 40 interposed between the top- and backsheets 20, 30 and a leakage-barrier sheet 50 interposed between the backsheet 30 and the absorbent body 40. As material for the top- and backsheets 20, 30, a fibrous nonwoven fabric, more specifically, a spunlace fibrous nonwoven fabric having a mass per unit area in a range of about 30 to about 40 g/m$^2$ may be used. Preferably, the topsheet 20 is liquid-permeable but the backsheet 30 is coated on its non-body-side with a water-disintegrable resin so that the material strength thereof may be improved and at the same time the liquid-permeability may be inhibited. As such a water-disintegrable resin, for example, "AQ55S" (trade name) of Eastman Chemical Co. may be used.

The fibrous nonwoven fabric from which the top- and backsheets 20, 30 are formed has water-disintegrable property. As used herein, the expression "water-disintegrable fibrous nonwoven fabric" means the fibrous nonwoven fabric formed of mechanically entangled fibers each having a fiber length of 7 mm or less and adapted to be rapidly disintegrated from the mechanically entangled state in flushing water of the lavatory. Thus, a piping system should not be clogged if the top- and backsheets 20, 30 are disposed into the lavatory.

<Measurement of Fiber Length>

The fiber length of component fibers of the backsheet 30 is measured in conformity with JIS L 1015 8.4.1: Testing method for chemical fiber staple. Specifically, the pantiliner is immersed in toluene to elute an adhesive agent with which the respective sheets have been joined to one another, then the backsheet 30 is taken out and the fibers of this sheet are disentangled. To disentangle the fibers, the backsheet 30 is transferred together with 300 ml of water into a 300 ml beaker and shaken at 600+/−10 rpm with use of a magnetic stirrer. Alternatively, the backsheet 30 is transferred together with 1200 ml of water into a 2000 ml wide-mouth jar and shaken at 270+/−20 rpm with use of an appropriate shaker. The fiber length of the disintegrated fibers is measured by the method specified in the above-mentioned JIS. From the measured values, an average value+/−standard variation is calculated as the fiber length in the backsheet 30.

At least the constituent fibers of the backsheet 30 have an orientation extending in the longitudinal direction Y. The expression that the fibers have the orientation extending in the longitudinal direction Y means that a breaking strength in the transverse direction X is 75% or less of a breaking strength in the longitudinal direction Y. The orientation was measured according to the method described below.

<Measurement of Orientation>

Pieces each having a length dimension of 150 mm in the longitudinal direction Y and a length dimension of 25 mm in the transverse direction X were cut off the backsheet 30 to obtain longitudinal test pieces. In the same manner, pieces each having a length dimension of 25 mm in the longitudinal direction Y and a length dimension of 150 mm were cut off the backsheet 30 to obtain transverse test pieces. Measurement of breaking strength was conducted on these longitudinal test pieces and transverse test pieces. For the measurement, Tensile Tester (manufactured by Instron Co. Ltd.) was used. For the longitudinal pieces and the transverse test pieces, a spacing between a pair of grippers of the tester was set to 100 mm, with both ends in the longitudinal direction of the test piece gripped by the gripper, the test piece was pulled at a rate of 100 mm/min and the maximum tensile strength at the break point was measured. The measurement was conducted under WET condition wherein the measurement was made after the test piece had been immersed in water and under DRY condition wherein the measurement was made without immersing the test piece in water. The orientation value was calculated according to the following formula:

Maximum strength of transverse test piece/maximum strength of longitudinal test piece×100

According to this embodiment, the orientation measured under WET condition was 29% and the orientation measured under DRY condition was 36%, both values verifying that the test pieces have the orientation in the longitudinal direction.

The absorbent body 40 is the same to the top- and backsheets 20, 30 in shape as well as in size and may be formed of airlaid pulp having amass per unit area in a range of about 60 to about 80 g/m$^2$. Specifically, fluff wood pulp may be integrated together with the use of a spray binder to form the absorbent body 40. The absorbent body 40 formed in this manner is water-disintegrable and the integrated fluff wood pulp is broken up in flushing water of the lavatory without clogging the piping system.

The leakage-barrier sheet 50 is liquid-impermeable and, specifically, water-disintegrable tissue paper having a mass per unit area in a range of about 10 to about 20 g/m² and laminated with the use of polylactic acid may be used as the leakage-barrier sheet 50. The leakage-barrier sheet 50 has an area smaller than those of the top- and backsheets 20, 30 and the absorbent body 40 and has a substantially rectangular shape. The polylactic acid becomes low-molecular in the presence of water and, in consequence, the leakage-barrier sheet 50 as a whole is sufficiently water-disintegrable to be broken up in flushing water of the lavatory without clogging the piping system.

Though not illustrated, securing means such as a hot melt adhesive is distributed between the topsheet 20 and the absorbent body 40, between the absorbent body 40 and the leakage-barrier sheet 50 and between the leakage-barrier sheet 50 and the backsheet 30, respectively, to join them to each other. Along the inside of the both side edges 11 and the front and rear end edges 12, 13 of the pantiliner 1, the topsheet 20, the absorbent body 40 and the backsheet 30 are heated under a pressure to seal them together.

Referring to FIG. 4, the backsheet 30 is disposed on the non-body-side with adhesive regions in which the backsheet 30 may be attached to the wearer's garment such as undergarment. The adhesive regions include first adhesive regions 60 allocated adjacent to the imaginary longitudinal center line P-P as viewed in the transverse direction X and second adhesive regions 70 allocated on both sides of the first adhesive regions 60 so as to be spaced apart from the first adhesive regions 60 as viewed in the transverse direction X. To be disposed with the first and second adhesive regions 60, 70, for example, a hot melt adhesive may be used. In this embodiment, a water-insoluble adhesive such as a rubber-based hot melt adhesive and an olefin-based hot melt adhesive is used. In this regard, the use of a water-soluble adhesive is not excluded and both types of adhesive may be selectively used.

The first adhesive regions 60 include front first adhesive regions 61, rear first adhesive regions 63 and central first adhesive regions 62 wherein two or more adhesive regions are arranged in the transverse direction X in each of the respective rows. In the present embodiment, three adhesive regions are arranged in the transverse direction X in the respective adhesive regions 61, 62, 63, and the middle adhesive regions in the respective rows are allocated on the imaginary longitudinal center line P-P. The front first adhesive regions 61 have front end edges 61a and rear end edges 61b aligned in the transverse direction X, respectively. The central first adhesive regions 62 also have front end edges 62a and rear end edges 62b aligned in the transverse direction X, respectively. In the same manner, the rear first adhesive regions 63 have front end edges 63a and rear end edges 63b aligned in the transverse direction X, respectively.

A length dimension d1 in the longitudinal direction Y of the first adhesive region 60 is longer than the fiber length in the fibrous nonwoven fabric used as the backsheet 30 and shorter than 50.0 mm. The length dimension d1 is about 30.0 mm in the present embodiment. A spacing dimension d2 in the longitudinal direction Y between two rows of the first adhesive regions 60 being adjacent to each other in the longitudinal direction Y is in a range of about 5.0 to about 50.0 mm and preferably longer than the fiber length of the fibrous nonwoven fabric used as the backsheet 30. The spacing dimension d2 is about 17.6 mm in the present embodiment. A width dimension d3 in the transverse direction X of the first adhesive region 60 is about 3.0 mm and a spacing dimension d4 in the transverse direction X between the first adhesive regions 50 being adjacent to each other in the transverse direction X is in a range of about 3.0 to 10.0 mm and preferably shorter than the fiber length of the fibrous nonwoven fabric used as the backsheet 30. The spacing dimension d4 is about 5.0 mm in the present embodiment.

The second adhesive region 70 includes front second adhesive regions 71 and rear second adhesive regions 72. According to the present embodiment, two pairs of the front and rear second adhesive regions 71, 72 are spaced apart from each other in the longitudinal direction Y and allocated on straight lines extending substantially in parallel to the imaginary longitudinal center line P-P. A length dimension D1 in the longitudinal direction Y of the front and rear second adhesive regions 71, 72 is longer than the fiber length of the fibrous nonwoven fabric used as the backsheet 30 and shorter than 50.0 mm. This length dimension D1 is about 43.0 mm in the present embodiment. A spacing dimension D2 in the longitudinal direction Y between the front and rear adhesive regions 71, 72 is in a range of about 5.0 to about 50.0 mm and preferably longer than the fiber length of the fibrous nonwoven fabric used as the backsheet 30 This spacing dimension is about 28.6 mm in the present embodiment. A width dimension D3 in the transverse direction X of the respective adhesive regions 71, 72 is in a range of about 2.0 to 15.0 mm. In the present embodiment, this width dimension D3 is about 7.0 mm. A spacing dimension D4 in the transverse direction X between the first adhesive region 60 and the adjacent second adhesive region 70 is in a range of about 3.0 to about 10.0 mm and preferably shorter than the fiber length of the fibrous nonwoven fabric used as the backsheet 30. Such spacing dimension D4 is about 5.0 mm in the present embodiment.

The central first adhesive regions 62 are formed in a space area defined between the front second adhesive regions 71 and the rear second adhesive regions 72 so as be allocated nearer to the imaginary longitudinal center line than the front and rear second adhesive regions 71,72 as viewed in the transverse direction X. More specifically, the central first adhesive regions 62 are allocated between an imaginary line extending so as to flush with respective rear end edges 71b of the front second adhesive regions 71 in parallel to the imaginary transverse center line Q-Q and an imaginary line extending so as to flush with respective front end edges 72a of the rear second adhesive regions 72. The central first adhesive regions 62 may be selectively dimensioned so as to intersect with these imaginary lines or so as not to intersect with these imaginary lines.

According to the present embodiment, the front end edges 62a of the central first adhesive regions 62 are aligned in the transverse direction X with the rear end edges 71b of the front second adhesive regions 71 and the rear end edges 62b of the central first adhesive regions 62 are aligned in the transverse direction X with the front end edges 72a of the rear second adhesive regions 72. Specifically, the imaginary line extending in parallel to the imaginary transverse center line Q-Q and collinearly with the front end edges 62a extends so as to be collinear with the rear end edges 71b of the front second adhesive regions 71. The imaginary line extending in parallel to the imaginary transverse center line Q-Q and collinearly with the rear end edges 62b extends so as to be collinear also with the front end edges 72a of the rear second adhesive regions 72. In the front first adhesive regions 61, the front end edges 61a are positioned outboard of the front end edges 71a of the front second adhesive regions 71 as viewed in the longitudinal direction Y and the rear end edges 61*b* are out of alignment with the 71*a* of the front second adhesive regions 71 in the transverse direction X. In other words, the imaginary line extending collinearly with the rear end edges 61*b* and in parallel to the imaginary transverse center line Q-Q intersects with these front second adhesive regions 71. In a similar fashion, the rear end edges 63*b* of the rear first adhesive regions 63 are positioned outboard of the rear end edges 72*b* of the rear second adhesive regions 72 as viewed in the longitudinal direction Y. In other words, the imaginary line extending collinearly with the front end edges 63*a* and extending in parallel to the imaginary transverse center line Q-Q intersects with these rear second adhesive regions 72.

Outboard in the longitudinal direction Y of the front and rear first adhesive regions 61, 63, front and rear non-adhesive regions 64, 65 are formed. In the present embodiment, the front non-adhesive region 64 is formed to be longer in the longitudinal direction Y than the rear non-adhesive region 65 so as to assure an area larger than an area of the rear non-adhesive region 65.

The first and second adhesive regions 60, 70 as described above are covered with the release sheet 80 of the same shape and size as the top- and backsheets 20, 30. By peeling the release sheet 80 off the first and second adhesive regions 60, 70, these first and second adhesive regions 60, 70 may be exposed without deteriorating adhesive force thereof. When it is desired to wear the pantiliner 1, the pantiliner 1 may be attached to the wearer's undergarment through the intermediary of the exposed first and second adhesive regions 60, 70.

At least outboard in the longitudinal direction Y of the first adhesive regions 60, there are formed with the front and rear non-adhesive regions 64, 65 from which the release sheet 80 may be easily peeled off. Particularly, the front non-adhesive region 64 has its area larger than the area of the rear non-adhesive region 65 and facilitates the release sheet 80 to be pinched with the wearer's fingers to peel off this.

In the pantiliner 1 described above, the central first adhesive regions 62 are allocated in the space area defined between the front and rear second adhesive regions 71, 72 and, in consequence, the pantiliner 1 attached to the wearer's undergarments might rise up from the undergarment. Assuming that none of the central first adhesive regions 62 is formed in the space area defined between the front and rear second adhesive regions and this space area remains non-adhesive to the wearer's undergarment, this space area will rise up from the wearer's undergarments until this space area will be put in contact with the wearer's body, eventually causing skin problems such as eczema. Generally, the pantiliner 1 is liable to rise up adjacent to the imaginary transverse centerline Q-Q and, in view of this, it is desirable to form the adhesive region at least adjacent to the imaginary transverse centerline Q-Q.

According to the present embodiment, the second adhesive regions 70 allocated on the outer sides of the first adhesive regions 60 in the transverse direction X are dimensioned to be relatively large in the longitudinal direction Y as well as in the transverse direction X to improve the adhesive force to the wearer's undergarment, thereby preventing the pantiliner 1 from being peeled off and curled along the lateral edges 11. In this regard, it is also possible for the same purpose to enlarge the dimension of the second adhesive regions 70 only in the longitudinal direction Y and the transverse direction X.

The pantiliner 1 as described above is composed of the top- and backsheets 20, 30, the absorbent body 40 and the leakage-barrier sheet 50 all having a sufficient degree of water-disintegrable property to be thrown away into the lavatory after used. The used pantiliner 1 thrown into the lavatory is finely disintegrated in flushing water of the lavatory and the piping system of the lavatory should not be clogged. The backsheet 30 includes the first and second adhesive regions 60, 70 formed thereon and these adhesive regions are not easily disintegrated in flushing water. In consequence, the portions of the backsheet 30 provided with these adhesive regions 60, 70 are also not easily disintegrated. However, these adhesive regions 60, 70 are formed so as to be spaced apart from each other in the longitudinal direction Y as well as in the transverse direction X and the backsheet 30 should not stay as a chunk in the piping system.

The dimension in the longitudinal direction Y of the first and second adhesive regions 60, 70 is longer than the fiber length of the backsheet 30 and shorter than 50 mm and consequently the fragments of the backsheet 30 respectively including the adhesive regions 60, 70 are sufficiently small to flow smoothly through the piping system even when these fragments of the backsheet 30 including the adhesive regions are not finely disintegrated in flushing water. Assuming that the dimension in the longitudinal direction Y of the first and second adhesive regions 60, 70 exceeds 50 mm, the fragments of the backsheet 30 respectively including the adhesive regions 60, 70 relatively long in the longitudinal direction Y might remain not disintegrated and these fragments might be entangled with each other to form a chunk causing clogging of the piping system. In contrast, if the dimension as described above is shorter than the fiber length of the backsheet 30, some of the fibers underlying the first and second adhesive regions 60, 70 of the backsheet 30 might dissociate from the backsheet 30 and attached to the wearer's undergarment together with the adhesive agent. However, the first and second adhesive regions 60, 70 may be dimensioned to be longer than the fiber length in the first and second adhesive regions 60, 70 to resolve such inconvenience, and to assure the pantiliner 1 to be attached to the wearer's undergarment. In addition, by orienting the component fibers of the backsheet 30 in the longitudinal direction Y and forming the first and second adhesive regions 60, 70 so as to extend in the longitudinal direction Y, it is possible to inhibit the undesirable dissociation of the fibers more reliably.

The spacing dimension d2 in the longitudinal direction Y between two rows of the first adhesive regions 60 being adjacent to each other in the longitudinal direction Y and the spacing dimension D2 in the longitudinal direction Y between the front and rear adhesive regions 71, 72 are preferably larger than the fiber length of the component fibers in the fibrous nonwoven fabric used as the backsheet 30. By dimensioning in this manner, it is assured to prevent the adhesive regions arranged in alignment with each other in the longitudinal direction Y from becoming contiguous to each other under an influence of the component fibers of the backsheet 30 oriented in the longitudinal direction Y. In this way, the adhesive regions arranged on the backsheet 30 to be in alignment with each other in the longitudinal direction Y are easily separated from each other in the flushing water and these adhesive regions might be entangled together to form a chunk remaining in the piping system.

The spacing dimension d4 in the transverse direction X between each pair of the adjacent first adhesive regions 60 and the spacing dimension D4 in the transverse direction X between each pair of the adjacent second adhesive region 70 and the first adhesive region 60 are preferably smaller than the fiber length of component fibers in the fibrous nonwoven fabric used as the backsheet 30. In the backsheet 30, the component fibers are oriented in the longitudinal direction Y and it is unnecessary to widen the spacing dimensions d4 and D4 so as to be larger than the length dimension of the fiber length in the backsheet 30. Even if the spacing dimensions as described above are shorter than the fiber length of the component fibers in the backsheet 30, it is possible to break up the continuity in the transverse direction X between each pair of the adjacent first adhesive regions 60 or each pair of the adjacent first and second adhesive regions 60, 70 in the flashing water. As an additional advantageous effect obtained by closing up the spacing dimensions between each pair of the adjacent first adhesive regions 60 and the spacing dimension between each pair of the first adhesive region 60 and the adjacent second adhesive region 70, a total adhesive area on the backsheet 30 as a whole can be enlarged and whereby an adhesive force to the wearer's undergarment may be improved.

While the respective rear end edges 71b of the front second adhesive regions 71 are aligned with the respective front end edges 62a of the central first adhesive regions 62 in the transverse direction X according to the present embodiment, it is also possible to arrange these adhesive regions in such a manner that the respective front end edges 62a are out of alignment with the respective rear end edges 71 in the longitudinal direction Y. In such a case, a spacing dimension between the rear end edge 71b and the associated front end edge 62 is preferably in a range of about 1.0 to about 5.0 mm. In the present invention, the central first adhesive regions 62 are allocated in the space area defined between the front second adhesive regions 71 and the rear second adhesive regions 72 and whereby it is possible to prevent the space area defined between these front and rear second adhesive regions 71, 72 from rising up above the wearer's undergarment. The respective dimensions may be selectively determined so long as such advantageous effect is ensured.

According to this embodiment, the first adhesive region 60 includes a plurality of adhesive regions arranged in the transverse direction X and the second adhesive region 70 includes two adhesive regions allocated outboard in the transverse direction X of the front and rear first adhesive regions. In these adhesive regions, each of the second adhesive regions 70 is formed so as to have its dimension in the transverse direction X larger than that of the first adhesive regions 60 and whereby the pantiliner 1 may be reliably attached to the wearer's undergarment. In addition, a plurality of the first adhesive regions 60 and a plurality of the second adhesive regions 70 are arranged in the transverse direction X so as to be spaced apart from each other and whereby the water-disintegrable property may be reliably maintained. In this regard, the number and the dimension of the first adhesive regions 60 in the longitudinal direction Y and in the transverse direction X as well as the number and the dimension of the second adhesive regions 70 in the longitudinal direction Y and in the transverse direction X are not limited to those in the embodiment described hereinbefore but may be appropriately selected.

Figure 5:
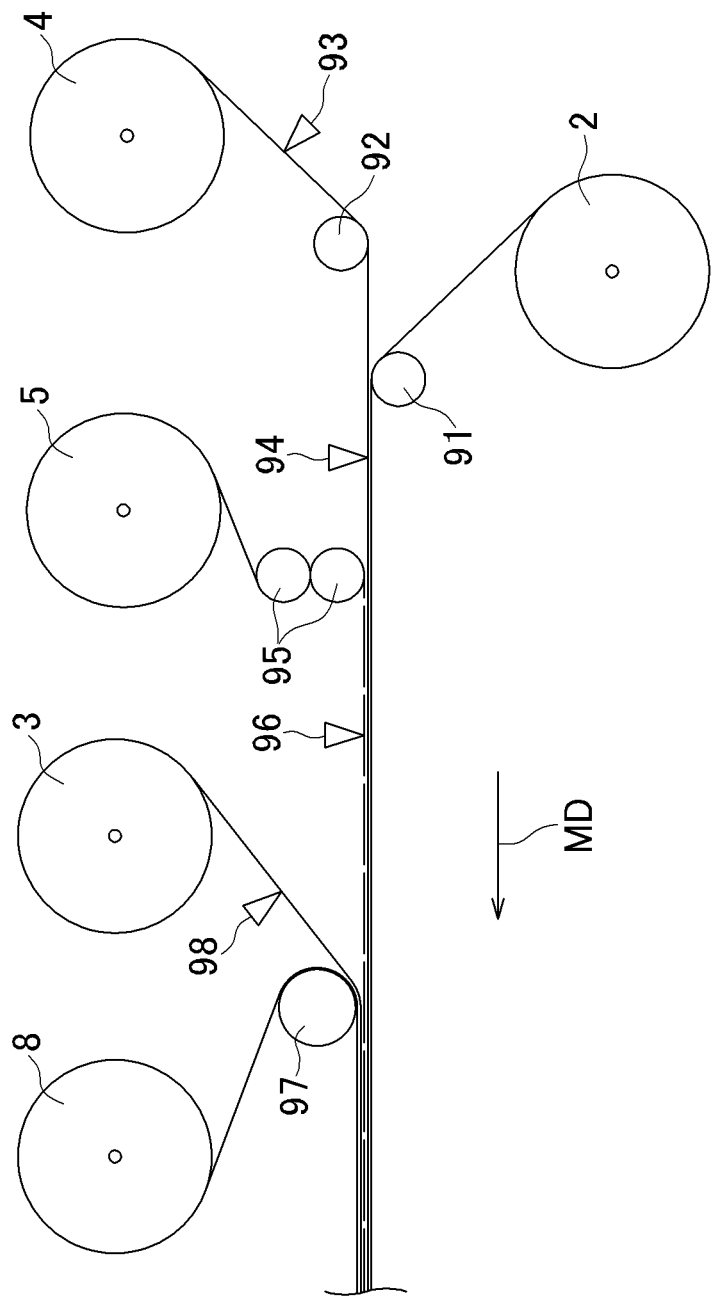
FIG. 5 is a schematic diagram illustrating a production process for the absorbent article.
Figure 6:
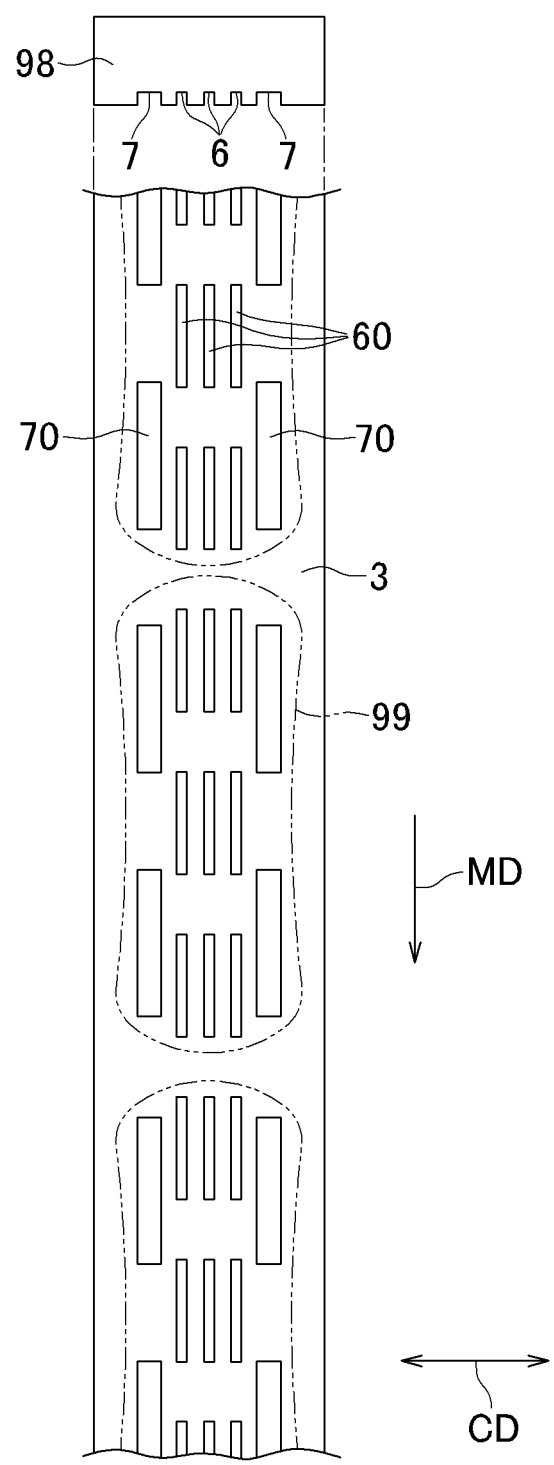
FIG. 6 is a diagram illustrating a process of forming adhesive zones.

The pantiliner as has been described hereinabove is manufactured by a method as described hereunder with reference to the accompanying drawings. FIG. 5 is a schematic diagram illustrating the method for producing the pantiliner 1. FIG. 6 is a diagram illustrating a step in which the first and second adhesive regions 60, 70 are formed and schematically illustrating a coater 98 so that a positional relation between nozzles and adhesive regions may be understood.

Referring to FIG. 5, a first fibrous web 2 to form the topsheet 20 is transported via a first roller 91 in a machine direction MD. An absorbent web 4 to form the absorbent body 40 is transported via a second roller 92 in the machine direction MD. The absorbent web 4 is coated by a coater 93 with a hot melt adhesive and laminated on the first web 2 and secured thereto. A coater 94 distributes hot melt adhesive onto a surface of the absorbent web 4 opposite to its surface being in face-to-face relationship with the first fibrous web 2. A leakage-barrier film 5 as material of the leakage-barrier sheet 50 is transported via a third roller 95 in the machine direction MD, laminated on the absorbent web 4 and bonded thereto. In this regard, the leakage-barrier film 5 is preliminarily cut in the machine direction MD and then transported via the third roller 95 to the absorbent web 4.

A coater 96 distributes a hot melt adhesive to a surface of the leakage-barrier film 5 opposite to its surface being in face-to-face relationship with the absorbent web 4. A second fibrous web 3 as material for the backsheet 30 is transported via a fourth roller 97 in the machine direction and MD and laminated on the leakage-barrier film 5 through the intermediary of hot melt adhesive and bonded thereto. The hot melt adhesive distributed by the coaters 93, 94, 96 is, for example, evenly distributed substantially over the entire area of the respective webs or the film by spray coating.

A coater 98 distribute a hot melt adhesive to a surface of the second fibrous web 3 opposite to its surface in face-to-face relationship with the leakage-barrier film 5 to form the first and second adhesive regions 60, 70. As illustrated in FIG. 6, the coater 98 has first nozzles 6 serving to form the first adhesive region 60 and second nozzles 7 lying on both outsides of the first nozzles 6 as viewed in a cross direction CD being orthogonal to the machine direction MD. This means that the same coater is provided with the first nozzles 6 and the second nozzles 7. The hot melt adhesive distributed from these first and second nozzles 6, 7 make it possible to form linear and continuous adhesive regions. A dimension in the CD direction of the discharge opening of the second nozzles 7 is larger than that of the first nozzles 6. The hot melt adhesive discharge timings of the first nozzles 6 and the second nozzles 7 separately controlled by separately prepared programs to form the first and second adhesive regions 60, 70 having different dimensions in the longitudinal direction Y as well as in the transverse direction. In this way, according to the present embodiment, it is possible to form the first and second adhesive regions 60, 70 having patterns with the use of the single coater. Consequently, it is unnecessary to increase the number of the coaters in order to form the adhesive regions having different patterns and, in consequence, production cost can be correspondingly reduced. Additionally, the first and second adhesive regions 60, 70 can be formed at once with no loss of production time.

Referring again to FIG. 5, the release web 8 as material for the release sheet 80 is laminated on the second fibrous web 3 which was provided with the first and second adhesive regions 60, 70 by the coater 98. The release web 8 is bonded to the second fibrous web 3 through the intermediary of the first and second adhesive regions 60, 70. Such laminate web is cut by a cutter (not shown) along an imaginary line 99 indicated in FIG. 6 to form the individual pantiliners 1.

The laminate web as described above is formed in a manner that the first and second adhesive regions 60, 70 do not overlap the imaginary line 99. In consequence, it is possible to prevent adhesive agent of the first and second adhesive regions 60, 70 from adhering to the cutter blade. The continuous laminate may be cut in this manner to form a large amount of the pantiliners 1 in a small amount of time.

The present invention described above may be arranged in at least one or more of the following features:

The present invention includes first and second aspects.

The first aspect relates to an improved absorbent article as described below. An absorbent article 1 has a longitudinal direction Y and a transverse direction X and includes a body-side, non-body-side opposite to the body-side, a water-disintegrable topsheet 20 lying on the body-side, a water-disintegrable backsheet 30 lying on the non-body-side, a water-disintegrable absorbent body 40 interposed between these top- and backsheets 20, 30 and adhesive regions 60, 70 formed on the non-body-side of the backsheet 30 and through which the backsheet 30 is attachable to a wearer's undergarment.

In the absorbent article 1 according to the first aspect, the backsheet 30 is formed of a fibrous nonwoven fabric of which component fibers have an orientation extending in the longitudinal direction Y. The adhesive regions include first adhesive regions 60 extending in the longitudinal direction Y and second adhesive regions 70 allocated on both outer sides in the transverse direction X of the first adhesive regions 60 so as to be spaced apart from the first adhesive regions 60 in the transverse direction X. At least apart of the first adhesive regions 60 is allocated in a space area defined in the longitudinal direction between the second adhesive regions 70.

The first aspect may include at least following embodiments.

(1) Respective length dimensions in the longitudinal direction Y of the adhesive regions 60, 70 may be set to be longer than a fiber length of component fibers in a fibrous nonwoven fabric as material of the backsheet 30.

(2) The first adhesive regions 60 may include front first adhesive regions 61, rear first adhesive regions 63 and central adhesive regions 62 allocated between the front and rear adhesive regions 61, 63.

(3) The second adhesive regions 70 may have front second adhesive regions 71 and rear second adhesive regions 72.

(4) A width dimension in the transverse direction X of the first and second adhesive regions 60, 70 may be in a range of 2.0 to 15.0 mm.

(5) A space dimension in the longitudinal direction Y between the first and second adhesive regions 60, 70 may be longer than a fiber length of component fibers in a fibrous nonwoven fabric as material of the backsheet.

(6) A space dimension in the transverse direction X between the first and second adhesive regions 60, 70 may be shorter than the fiber length of the component fibers in the fibrous nonwoven fabric as material of the backsheet.

(7) A length dimension in the longitudinal direction Y of the second adhesive regions 70 may be longer than a length dimension in the longitudinal dimension of the first adhesive regions 60.

(8) Non-adhesive regions 64, 65 may be formed on the outer sides in the longitudinal direction Y of the first adhesive regions 60.

(9) A liquid-impermeable leakage-barrier sheet 50 may be interposed between the absorbent body 40 and the backsheet 30 and at least one of the first and second adhesive regions 60, 70 may be allocated to overwrap both side edges of the leakage-barrier sheet 50.

The second aspect relates to improvement in a method of producing the absorbent article as described above. Namely, a method for producing the absorbent article including the steps of: transporting first fibrous web in a machine direction MD; laminating an absorbent web 4 on the first fibrous web 2 and securing them to each other; laminating second fibrous web 3 on the first fibrous web 2 through the absorbent web 4 and securing them to each other; forming adhesive regions on a surface of one of the first fibrous web 2 and the second fibrous web 3 opposite to the absorbent web 4; and laminating a release sheet 8 on the adhesive regions 60, 70 and cutting a laminate composed of the first and second fibrous webs 2, 3, the absorbent web 4 and the release sheet 8.

In the method for producing the absorbent article, the second invention lies in that an adhesive coater 98 having first nozzles 6 arranged in the cross direction being orthogonal to the machine direction MD and second nozzles 7 allocated outboard in the cross direction CD of the first nozzles distribute adhesive agent and thereby forms the adhesive regions 60, 70.

The second invention may include at least an embodiment as described below.

The laminate may be cut between each pair of the adjacent adhesive regions 60, 70 arranged in the longitudinal direction Y so as to be spaced apart from each other.

The respective constituent elements of the pantiliner 1 as an example of the absorbent articles are not limited to those described in this description but other various types of material widely used in the relevant technical field may be used without limitation. The terms "first", "second", "third" and "fourth" used in the description of the present invention are used merely to distinguish the similar elements or similar positions.

REFERENCE SIGNS LIST 1 absorbent article (pantiliner)
20 topsheet
30 backsheet
40 absorbent body
50 leakage-barrier sheet
60 first adhesive region
61 front first adhesive region
62 central first adhesive region
63 rear first adhesive region
64 non-adhesive region
65 non-adhesive region
70 second adhesive region
71 front second adhesive region
72 rear second adhesive region
80 release sheet
2 first fibrous web
3 second fibrous web
4 absorbent web
5 leakage-barrier film
6 first nozzle
7 second nozzle
8 release web
98 coater
X transverse direction
Y longitudinal direction
P-P imaginary longitudinal center line
Q-Q imaginary transverse center line
MD machine direction
CD cross direction

The invention claimed is:

1. An absorbent article having a longitudinal direction and a transverse direction, and including:
   a body-side;
   a non-body-side opposite to the body-side;
   a water-disintegrable topsheet lying on the body-side;

a water-disintegrable backsheet lying on the non-body-side;

a water-disintegrable absorbent body interposed between these top- and backsheets; and adhesive regions formed on the non-body-side of the backsheet and through which the backsheet is attachable to a wearer's undergarment, wherein:

the backsheet is formed of a fibrous nonwoven fabric of which component fibers have an orientation extending in the longitudinal direction and a fiber length, the adhesive regions include first adhesive regions extending in the longitudinal direction and second adhesive regions allocated on both outer sides in the transverse direction of the first adhesive regions so as to be spaced apart from the first adhesive regions in the transverse direction and at least part of the first adhesive regions is allocated in a space area defined in the longitudinal direction between the second adhesive regions, and a space dimension in the transverse direction between the first and second adhesive regions is shorter than the fiber length of the component fibers in the fibrous nonwoven fabric of the backsheet.

2. The absorbent article according to claim 1, wherein respective length dimensions in the longitudinal direction of the first and second adhesive regions are longer than the fiber length of component fibers in the fibrous nonwoven fabric of the backsheet.

3. The absorbent article according to claim 2, wherein the second adhesive regions have front second adhesive regions and rear second adhesive regions.

4. The absorbent article according to claim 2, wherein a width dimension in the transverse direction of the first and second adhesive regions is in a range of 2.0 to 15.0 mm.

5. The absorbent article according to claim 2, wherein the first adhesive regions include front first adhesive regions, rear first adhesive regions and central first adhesive regions allocated between the front and rear first adhesive regions.

6. The absorbent article according to claim 5, wherein the second adhesive regions have front second adhesive regions and rear second adhesive regions.

7. The absorbent article according to claim 5, wherein a width dimension in the transverse direction of the first and second adhesive regions is in a range of 2.0 to 15.0 mm.

8. The absorbent article according to claim 1, wherein the first adhesive regions include front first adhesive regions, rear first adhesive regions and central first adhesive regions allocated between the front and rear first adhesive regions.

9. The absorbent article according to claim 8, wherein the second adhesive regions have front second adhesive regions and rear second adhesive regions.

10. The absorbent article according to claim 8, wherein a width dimension in the transverse direction of the first and second adhesive regions is in a range of 2.0 to 15.0 mm.

11. The absorbent article according to claim 1, wherein the second adhesive regions have front second adhesive regions and rear second adhesive regions.

12. The absorbent article according to claim 11, wherein a width dimension in the transverse direction of the first and second adhesive regions is in a range of 2.0 to 15.0 mm.

13. The absorbent article according to claim 1, wherein a width dimension in the transverse direction of the first and second adhesive regions is in a range of 2.0 to 15.0 mm.

14. The absorbent article according to claim 1, wherein a space dimension in the longitudinal direction between the first and second adhesive regions is longer than the fiber length of component fibers in the fibrous nonwoven fabric of the backsheet.

15. The absorbent article according to claim 1, wherein a length dimension in the longitudinal direction of the second adhesive regions is longer than a length dimension in the longitudinal dimension of the first adhesive regions.

16. The absorbent article according to claim 1, wherein non-adhesive regions are formed on the outer sides in the longitudinal direction of the first adhesive regions.

17. The absorbent article according to claim 1, wherein a liquid-impermeable leakage-barrier sheet is interposed between the absorbent body and the backsheet and at least one of the first and second adhesive regions extends beyond both lateral side edges of the leakage-barrier sheet in the lateral direction.

* * * * *